(12) United States Patent
Hara et al.

(10) Patent No.: US 10,479,681 B2
(45) Date of Patent: Nov. 19, 2019

(54) FLUORINATING AGENT

(71) Applicants: DAIKIN INDUSTRIES, LTD., Osaka (JP); NATIONAL UNIVERSITY CORPORATION HOKKAIDO UNIVERSITY, Hokkaido (JP)

(72) Inventors: Shoji Hara, Sapporo (JP); Yosuke Kishikawa, Osaka (JP); Atsushi Shirai, Osaka (JP); Takashi Namikawa, Osaka (JP); Sumi Ishihara, Osaka (JP)

(73) Assignees: DAIKIN INDUSTRIES, LTD., Osaka (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 0 days.

(21) Appl. No.: 16/261,737

(22) Filed: Jan. 30, 2019

(65) Prior Publication Data

US 2019/0152779 A1    May 23, 2019

Related U.S. Application Data

(62) Division of application No. 15/026,349, filed as application No. PCT/JP2014/076455 on Oct. 2, 2014, now Pat. No. 10,233,080.

(30) Foreign Application Priority Data

Oct. 2, 2013 (JP) .................... 2013-207010
Aug. 28, 2014 (JP) .................... 2014-173792

(51) Int. Cl.

| | | |
|---|---|---|
| C01B 7/24 | (2006.01) | |
| C01D 3/02 | (2006.01) | |
| C01D 13/00 | (2006.01) | |
| C07C 17/354 | (2006.01) | |
| C07C 17/361 | (2006.01) | |
| C07C 41/22 | (2006.01) | |
| C07C 45/63 | (2006.01) | |
| C07C 45/67 | (2006.01) | |
| C07C 67/307 | (2006.01) | |
| C07C 67/333 | (2006.01) | |
| C07C 209/74 | (2006.01) | |
| C07C 231/12 | (2006.01) | |
| C07C 319/20 | (2006.01) | |
| C07D 209/10 | (2006.01) | |
| C07D 309/10 | (2006.01) | |
| C07D 493/04 | (2006.01) | |

(52) U.S. Cl.
CPC .................. *C01B 7/24* (2013.01); *C01D 3/02* (2013.01); *C01D 13/00* (2013.01); *C07C 17/354* (2013.01); *C07C 17/361* (2013.01); *C07C 41/22* (2013.01); *C07C 45/63* (2013.01); *C07C 45/673* (2013.01); *C07C 67/307* (2013.01); *C07C 67/333* (2013.01); *C07C 209/74* (2013.01); *C07C 231/12* (2013.01); *C07C 319/20* (2013.01); *C07D 209/10* (2013.01); *C07D 309/10* (2013.01); *C07D 493/04* (2013.01); *C07C 2603/86* (2017.05)

(58) Field of Classification Search
CPC .......................................................... C01B 7/24
See application file for complete search history.

(56) References Cited

U.S. PATENT DOCUMENTS

2004/0245505 A1   12/2004 Yoneda et al.
2011/0008682 A1   1/2011  Koh et al.

FOREIGN PATENT DOCUMENTS

| JP | 2002-308884 | 10/2002 |
|---|---|---|
| JP | 2005-522398 | 7/2005 |
| JP | 2007-008825 | 1/2007 |
| JP | 2009-206071 | 9/2009 |
| WO | 03/086969 | 10/2003 |

OTHER PUBLICATIONS

International Search Report dated Jan. 6, 2015 in International (PCT) Application No. PCT/JP2014/076455.
Sharpe et al., "Chemistry of the Inter-halogen Compounds. Part I. The Reaction of Bromine Trifluoride with Metallic Halides", Journal of the Chemical Society, 1948, pp. 2135-2138.
Ivlev et al., "Physical-chemical bases of potassium fluorobromate(III) synthesis from KF and $BrF_3$", Abstracts of Papers, 242nd ACS National Meeting & Exposition, 2011.
Hara et al., "$IF_5$-pyridine-HF: air- and moisture-stable fluorination reagent", Tetrahedron, vol. 68, Oct. 2, 2012, pp. 10145-10150.
Mitkin et al., "Application of potassium tetrafluorobromate to the rapid decomposition and determination of noble metals in chromites and related materials", Spectrochimica Acta Part B, vol. 58, (2003), pp. 297-310.
Extended European Search Report dated Feb. 15, 2017 in corresponding European Application No. 14850310.5.
Sergey Ivlev et al., "Tetrafluorobromates for Urban Mining of Nobel Metals: A Case Study on Iridium Metal", European Journal of Inorganic Chemistry, 2013, pp. 4984-4987.
Sergey Ivlev et al., "On Tetrafluorobromates(III): Crystal Structures of the Dibromate $CsBr_2F_7$ and the Monobromate $CsBrF_4$", Journal of Inorganic and General Chemistry, vol. 639, No. 15, 2013, pp. 2846-2850.

(Continued)

*Primary Examiner* — Shawquia Jackson
(74) *Attorney, Agent, or Firm* — Wenderoth, Lind & Ponack, L.L.P.

(57) ABSTRACT

An object of the present invention is to provide a novel substance that has a high reactivity as a fluorinating agent, is effectively used in various fluorination reactions, and is safely handled even in air. As the solution for achieving this object, the present invention provides a complex obtained by reacting bromine trifluoride with at least one metal halide selected from the group consisting of halogenated metals and halogenated hydrogen metals in a nonpolar solvent. This complex serves as a fluorinating agent that provides excellent fluorination performance and that is stable in air.

7 Claims, No Drawings

(56) References Cited

OTHER PUBLICATIONS

Karl O. Christe et al., "The Tetrafluorobromate(III) Anion, $BrF_4^-$", Inorganic Chemistry, vol. 9, No. 8, 1970, pp. 1852-1858.
V.N. Mitkin et al., "New technique for the determination of trace noble metal content in geological and process materials", Spectrochimica Acta Part B, vol. 58, 2003, pp. 311-328.
Sakurai. Document No. 77:169111, retrieved from CAPLUS; (1972).

FLUORINATING AGENT

TECHNICAL FIELD

The present invention relates to a novel complex, a method for producing the novel complex, and a fluorinating agent.

BACKGROUND ART

Fluorine compounds are extremely important as, for example, functional materials, compounds for medicines and agrochemicals, electronic materials, and other various chemical products, as well as the intermediates of these.

Fluoride, hydrogen fluoride, sulfur tetrafluoride, etc., have been used as fluorinating agents to obtain a target fluorine compound by fluorinating a variety of organic compounds as a starting material. These fluorinating agents, however, are difficult to handle due to, for example, their toxicity, corrosiveness, and explosion risk at the time of reaction, and thus require special devices or techniques.

A reaction for introducing a fluorine atom into an organic compound by using nucleophilic substitution with fluoride ion has recently been developed, in addition to various fluorinating agents used for the reaction.

Iodine pentafluoride ($IF_5$), for example, is known as a powerful fluorinating agent with high oxidizing power; however, this is a dangerous liquid fluorinating agent because it reacts with moisture in air and decomposes while generating HF. Non-patent Literature 1 recently reported that $IF_5$ having such features becomes a stable white solid in air when mixed with pyridine-HF and is effective for fluorination of various sulfur compounds.

Further, bromine trifluoride ($BrF_3$) is a liquid that has oxidizing power stronger than that of $IF_5$. $BrF_3$ is usable in fluorination of various kinds of substrates, and is used, for example, to produce uranium hexafluoride in nuclear fuel processing. However, $BrF_3$ is a toxic and corrosive liquid, and is a strong irritant to the eyes or skin. In air, $BrF_3$ has the problems of decomposing within a short period of time, generating hydrogen fluoride, and the like. Further, $BrF_3$ reacts vigorously with general-purpose solvents, such as methylene chloride, at room temperature. Thus, the solvent used with $BrF_3$ is limited when $BrF_3$ is used as a fluorinating agent. Accordingly, the use of $BrF_3$ requires special knowledge and devices, and the practical use of $BrF_3$ in a wide scope has not yet been achieved at present, although $BrF_3$ has a high reactivity as a fluorinating agent.

CITATION LIST

Non-Patent Literature

Non-patent literature 1: S. Hara, M. Monoi, R. Umemura, C. Fuse, Tetrahedron, 2012, 68, 10145-10150.

SUMMARY OF INVENTION

Technical Problem

The present invention has been accomplished in view of the state of the prior art described above, and its primary object is to provide a novel substance that has a high reactivity as a fluorinating agent, is effectively used in various fluorination reactions, and also is safely handled even in air.

Solution to Problem

The present inventors conducted extensive research to achieve the object and found that a complex that is a reaction product obtained by reacting bromine trifluoride ($BrF_3$), which is considered to be a difficult-to-handle fluorinating agent because it decomposes in air within a short period of time, with a halogenated metal or a halogenated hydrogen metal is safely handled in air, and provides excellent performance as a fluorinating agent in various fluorination reactions. The present invention has thus been accomplished.

More specifically, the present invention provides the following novel complex, fluorinating agent, and method for producing a fluorinating agent.

Item 1. A complex consisting of bromine trifluoride and at least one metal halide selected from the group consisting of halogenated metals and halogenated hydrogen metals.

Item 2. The complex according to Item 1, wherein the complex exhibits an exothermic decomposition onset temperature in nitrogen of 40° C. or higher.

Item 3. The complex according to Item 1 or 2, wherein the complex is a reaction product obtained by mixing bromine trifluoride with at least one metal halide selected from the group consisting of halogenated metals and halogenated hydrogen metals, in a nonpolar solvent.

Item 4. The complex according to Item 3, wherein the reaction product is obtained by reacting 0.5 mol or more of the metal halide, per mol of bromine trifluoride.

Item 5. The complex according to any one of Items 1 to 4, wherein the metal halide is at least one member selected from the group consisting of a halogenated metal represented by the formula: MX, wherein M is $M^1$ or $(M^2)_{1/2}$), $M^1$ is an alkali metal, and $M^2$ is an alkaline earth metal, and X is a halogen atom; and a halogenated metal represented by the formula: $MHX^2$, wherein M and X are as defined above.

Item 6. The complex according to any one of Items 1 to 5, wherein the metal halide is at least one potassium halide selected from the group consisting of halogenated potassium and halogenated hydrogen potassium.

Item 7. The complex according to any one of Items 1 to 6, wherein the metal halide is at least one potassium fluoride selected from the group consisting of fluorinated potassium and fluorinated hydrogen potassium.

Item 8. A fluorinating agent consisting of the complex of any one of Items 1 to 7.

Item 9. A method for producing the complex of any one of Items 1 to 7, the method comprising:
mixing bromine trifluoride with at least one metal halide selected from the group consisting of halogenated metals and halogenated hydrogen metals, in a nonpolar solvent; and
collecting the resulting solids content.

Examples of "halogen" as used in the present specification include fluorine, chlorine, bromine, iodine, and the like.

Examples of "alkyl" as used in the present specification include lower alkyl, such as $C_{1-6}$ alkyl (e.g., methyl, ethyl, propyl, isopropyl, butyl, isobutyl, sec-butyl, tert-butyl, pentyl, neopentyl, and hexyl).

Examples of "alkoxy" as used in the present specification include an R—O-group (R represents alkyl) and the like.

Examples of "ester" as used in the present specification include an R—CO—O-group (R represents alkyl), a R—O—CO-group (R represents alkyl), and the like.

Examples of "amide" as used in the present specification include a $R^aR^bN$—CO-group ($R^a$ and $R^b$ each independently represent hydrogen or alkyl) and a $R^a$—CO—$NR^b$-group ($R^a$ and $R^b$ each independently represent hydrogen or alkyl).

Examples of "substituted or unsubstituted amino" as used in the present specification include a $R^aR^bN$-group ($R^a$ and $R^b$ each independently represent hydrogen, alkyl, or phenyl that may be substituted with one or more substituents), and the like.

Examples of the "phenyl that may be substituted with one or more substituents" include phenyl that may be substituted with one or more substituents selected from the group consisting of halogen, lower alkyl, alkoxy, ester, amide, and amino.

The following describes the novel complex of the present invention and a fluorinating agent consisting of this complex.

Fluorinating Agent

The fluorinating agent of the present invention consisting of a complex of bromine trifluoride ($BrF_3$) and at least one metal halide selected from the group consisting of halogenated metals and halogenated hydrogen metals. This complex is obtained by reacting bromine trifluoride ($ErF_3$) with at least one metal halide selected from the group consisting of halogenated metals and halogenated hydrogen metals. The complex is a novel substance that is not a mere mixture of a metal halide and bromine trifluoride, and is characterized, for example, in exhibiting an exothermic decomposition onset temperature in nitrogen of 40° C. or higher.

As described above, bromine trifluoride decomposes in air within a short period of time and is difficult to handle. However, in the fluorinating agent of the present invention, bromine trifluoride forms a complex with at least one metal halide selected from the group consisting of halogenated metals and halogenated hydrogen metals, rather than simply being mixed with the at least one metal halide. Therefore, the complex, i.e., an active ingredient of the fluorinating agent of the present invention, differs from bromine trifluoride as a simple substance. The complex is characterized in exhibiting an exothermic decomposition onset temperature in nitrogen of 40° C. or higher, and is stable in air at ordinary temperature. Further, the complex is characterized in having a low reactivity with methylene chloride, which is a general-purpose solvent, and is easy to handle. This complex exhibits an exothermic decomposition onset temperature in nitrogen of preferably 100° C. or higher, and more preferably 150° C. or higher.

Among generally commercially available fluorinating agents, many are thermally unstable. For example, DAST (N,N-diethylaminosulfur trifluoride), which is widely used as a fluorinating agent in organic synthesis reactions, exhibits an exothermic decomposition onset temperature of about 85° C. Further, DAST is known to explosively decompose at 147° C. (W. J. Middleton et al., J. Fluorine Chem., 1989, 42, 137-143). In contrast, the complex of the present invention has an exothermic decomposition onset temperature in nitrogen of 40° C. or higher, and, for example, the $BrF_3$-$2KHF_2$ complex obtained in Example 1 described later exhibits an exothermic decomposition onset temperature of 197° C., while the $BrF_3$-2KF complex obtained in Example 2 exhibited an exothermic decomposition onset temperature of 252° C., the substances of which are more safely used.

Additionally, compared with the reaction product of $IF_5$ and pyridine-HF mentioned above, the complex, i.e., an active ingredient of the fluorinating agent of the present invention, is an industrially highly useful fluorinating agent because the complex is inexpensive, has a high reactivity in various fluorination reactions, and enables the provision of a target fluorinated compound with a high yield.

The exothermic decomposition onset temperature of the complex of the present invention is a value measured in nitrogen atmosphere by using the following method.

Measuring method: TG/DTA
Sample amount: 9.5 mg
Temperature elevating condition: maintained at 20° C. for 10 minutes, followed by heating to 600° C. at a temperature elevation rate of 10° C./min The complex, i.e., an active ingredient of the fluorinating agent of the present invention, is obtained by reacting bromine trifluoride and at least one metal halide selected from the group consisting of halogenated metals and halogenated hydrogen metals that are used as starting materials, for example, in a nonpolar solvent.

Of the metal halides used as a starting material, the halogenated metals are compounds represented by the formula: MX, while the halogenated hydrogen metals are compounds represented by the formula: $MHX_2$.

In the formulae, M represents $M^1$ or $(M^2)_{1/2}$, and $M^1$ represents an alkali metal and $M^2$ represents an alkaline earth metal. Specific examples of alkali metals represented by $M^1$ include K, Li, Cs, Na, and the like. Specific examples of alkaline earth metals represented by $M^2$ include Ca, Mg, and the like.

X is halogen, and specific examples include fluorine, chlorine, and the like. Two Xs in the formula representing a halogenated hydrogen metal may be identical or different. These halogenated metals and halogenated hydrogen metals may be used singly or in a combination of two or more.

In the present invention, M is preferably an alkali metal and particularly preferably potassium for, in particular, their easy availability and the like. Therefore, a metal halide used for a reaction with bromine trifluoride is preferably at least one halogenated alkali metals and halogenated hydrogen alkali metals, and is more preferably at least one potassium halide selected from the group consisting of halogenated potassium and halogenated hydrogen potassium.

X is preferably a fluorine atom to obtain a target fluorinating agent with sufficient selectivity when used as a fluorinating agent. Therefore, in the present invention, a metal halide is particularly preferably at least one potassium fluoride selected from the group consisting of fluorinated potassium and fluorinated hydrogen potassium.

In the present invention, the metal halide is preferably a halogenated hydrogen metal because it has a high reactivity. Therefore, in the present invention, the metal halide is particularly preferably fluorinated hydrogen potassium.

The reaction between a metal halide and bromine trifluoride described above may be performed, for example, by mixing a metal halide and bromine trifluoride in a nonpolar solvent. However, the method for performing the reaction in a nonpolar solvent is an example of the method for producing the complex of the present invention, and the method for producing the complex of the present invention is not limited to the method for performing the reaction in a nonpolar solvent.

The nonpolar solvent may be any solvent as long as it does not react with bromine trifluoride used as a starting material. Examples of usable nonpolar solvents include methylene chloride, chloroform, hexane, heptane, pentane, cyclohexane, benzene, chlorobenzene, toluene, xylene, and the like. These solvents may be used singly or in a combination of two or more.

The concentration of bromine trifluoride in a nonpolar solvent is not particularly limited, as long as a homogeneous suspension is formed. The concentration may be, for example, about 0.05 to 2.0 g/mL.

The amount of the metal halide used is not particularly limited. The metal halide is usually used in an amount of about 0.5 mol or more, per mol of bromine trifluoride. The metal halide is preferably used in an equimolar or greater amount, relative to bromine trifluoride, so that no bromine trifluoride remains after the reaction. For example, the total amount of a halogenated metal represented by the formula: MX and a halogenated hydrogen metal represented by the formula: $MHX_2$ may be about 0.5 to 5 mol, preferably about 1 to 3 mol, and more preferably about 1 to 2 mol, per mol of bromine trifluoride.

According to one example of a specific reaction method, a container that does not react with bromine trifluoride, such as a Teflon (registered trademark) container, is used as a reactor, and a metal halide used as a starting material is homogeneously suspended in a nonpolar solvent, followed by the addition of a required amount of bromine trifluoride and sufficient stirring.

The reaction is preferably performed in an inert gas atmosphere, such as nitrogen or argon. The reaction is preferably performed at a sufficiently low temperature such that bromine trifluoride does not react with a solvent. The specific reaction temperature may be set according to, for example, the melting point of the solvent to be used. The temperature may be higher than the melting point of the solvent, and at the same time, within a range that does not cause the reaction with bromine trifluoride. When, for example, methylene chloride is used as a solvent, the reaction temperature may be about −85 to −50° C.

The reaction time varies depending on, for example, the reaction temperature and the type of the fluorinated metal to be used. It is usually about 15 minutes to 5 hours.

After performing the reaction by using the method described above, the temperature of the reaction solution is returned to room temperature, and the solids content, which is a reaction product, is collected. In this manner, a target complex of bromine trifluoride with at least one metal halide selected from the group consisting of halogenated metals and halogenated hydrogen metals is obtained. It is preferable to repeatedly wash the collected solids content with the used solvent until the washing solution is colorless.

Application of Fluorinating Agent

The complex of the present invention consisting of bromine trifluoride and at least one metal halide selected from the group consisting of halogenated metals and halogenated hydrogen metals is obtained by the method described above. This complex is useful as a fluorinating agent that has a high reactivity in fluorination reactions of various organic compounds, is easy to handle, and is stable in air at ordinary temperature.

The complex of the present invention serves as a fluorinating agent that is effectively used in previously known fluorination reactions of various organic compounds. The complex of the present invention enables yielding of a target fluorinated compound with a high yield, for example, through various fluorination reactions.

The following shows an example of fluorination reactions in which the complex of the present invention is effectively used as a fluorinating agent. However, fluorination reactions in which the complex of the present invention is effectively used as a fluorinating agent are not limited to these reactions.

In this specification, "alkyl" is, for example, lower alkyl.

In this specification, "lower alkyl" is, for example, $C_{1-6}$ alkyl.

In this specification, "cycloalkane" is, for example, $C_{1-10}$ cycloalkane.

(1) Desulfurization-Difluorination Reaction

The complex of the present invention may be used as a fluorinating agent in desulfurization-difluorination reactions. For example, following the reaction scheme below, a gem-difluoride is obtained by reacting the fluorinating agent with a benzyl sulfide compound.

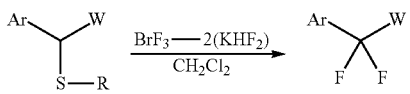

Examples of Ar in the benzyl sulfide compound used in the above reaction include substituted or unsubstituted phenyl. Examples of W include an ester residue ($-CO_2R$), an amide residue ($-CON(R)_2$), an acyl group ($-COR$), and the like. Examples of R include lower alkyl, substituted or unsubstituted phenyl, and the like. $BrF_3$-$2(KHF_2)$ represents a complex obtained by the reaction of 2 mol of $KHF_2$, per mol of $BrF_3$.

Examples of the "substituted or unsubstituted phenyl" represented by Ar include phenyl that may be substituted with one or more substituents selected from the group consisting of halogen, lower alkyl, alkoxy, ester, amide, and amino.

Examples of the "substituted or unsubstituted phenyl" represented by R include phenyl that may be substituted with one or more substituents selected from the group consisting of halogen, lower alkyl, alkoxy, ester, amide, and amino.

The reaction above may be performed in a nonpolar solvent, such as methylene chloride, chloroform, hexane, heptane, pentane, cyclohexane, benzene, chlorobenzene, toluene, and xylene. The reaction may be performed at about room temperature.

Specific reaction conditions may be set according to, for example, the type of the starting materials to be used and in a similar manner to the conditions for a known desulfurization-fluorination reaction.

Following the reaction scheme below, a gem-difluoride is also obtained by reacting the fluorinating agent with a thionoester compound.

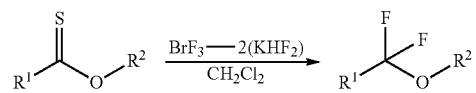

In the reaction scheme above, $R^1$ and $R^2$ are identical or different, and each represents substituted or unsubstituted phenyl, lower alkyl, cycloalkyl, or the like. $R^1$ and $R^2$, taken together, may form a cyclic structure. $BrF_3$-$2(KHF_2)$ represents a complex obtained by the reaction of 2 mol of $KHF_2$, per mol of $BrF_3$.

Examples of the "substituted or unsubstituted phenyl" represented by each of $R^1$ and $R^2$ include phenyl that may be substituted with one or more substituents selected from the group consisting of halogen, lower alkyl, alkoxy, ester, amide, and amino.

$R^1$ and $R^2$, taken together, may form, for example, a divalent group, such as an alkylene chain (e.g., $-CH_2-CH_2-CH_2-CH_2-$, $-CH_2-CH_2-CH_2-$).

The above reaction may also be performed in a nonpolar solvent, such as methylene chloride, chloroform, hexane, heptane, pentane, cyclohexane, benzene, chlorobenzene, toluene, and xylene. Specific reaction conditions may be set according to, for example, the type of the starting materials to be used, and based on the conditions for a known desulfurization-difluorination reaction.

(2) Desulfurization-Fluorination Reaction

The complex of the present invention may also be effectively used as a fluorinating agent in desulfurization-fluorination reactions of various sulfide compounds. For example, following the reaction scheme below, a gem-difluoride or a trifluoromethyl compound is obtained by reacting a sulfide compound, such as an orthothioester compound and a thioacetal compound, with the fluorinating agent of the present invention.

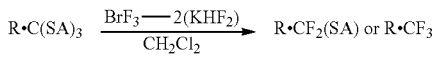

In the reaction scheme above, three As are identical or different, and each represents, for example, lower alkyl, substituted or unsubstituted phenyl, or the like. Of these lower alkyl groups, two alkyl groups, taken together, may form a cyclic structure. Examples of R include substituted or unsubstituted phenyl, a group: —$C(R^1)_2CO^2R^2$, and the like. $R^1$ and $R^2$ each represent lower alkyl.

Examples of the "substituted or unsubstituted phenyl" represented by A include phenyl that may be substituted with one or more substituents selected from the group consisting of halogen, lower alkyl, alkoxy, ester, amide, and amino.

Examples of the "substituted or unsubstituted phenyl" represented by R include phenyl that may be substituted with one or more substituents selected from the group consisting of halogen, lower alkyl, alkoxy, ester, amide, and amino.

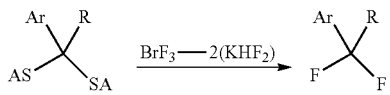

In the reaction scheme above, two As are identical or different, and each represents, for example, lower alkyl, substituted or unsubstituted phenyl, or the like. Examples of Ar include substituted or unsubstituted phenyl, substituted or unsubstituted naphthyl, adamantyl, and the like. Examples of R include hydrogen, lower alkyl, cycloalkyl, phenyl, and the like. R and Ar, taken together, may form a cyclic structure.

Examples of the "substituted or unsubstituted phenyl" represented by A include phenyl that may be substituted with one or more substituents selected from the group consisting of halogen, lower alkyl, alkoxy, ester, amide, and amino.

Examples of the "substituted or unsubstituted phenyl" represented by Ar include phenyl that may be substituted with one or more substituents selected from the group consisting of halogen, lower alkyl, alkoxy, ester, amide, and amino.

Examples of the "substituted or unsubstituted naphthyl" represented by Ar include naphthyl that may be substituted with one or more substituents selected from the group consisting of halogen, lower alkyl, alkoxy, ester, amide, and amino.

In each reaction scheme above, $BrF_3$-$2(KHF_2)$ represents a complex obtained by the reaction of 2 mol of $KHF_2$, per mol of $BrF_3$.

Each of the above reactions may be performed in a nonpolar solvent, such as methylene chloride, chloroform, hexane, heptane, pentane, cyclohexane, benzene, chlorobenzene, toluene, and xylene. Specific reaction conditions may be set according to, for example, the type of the starting materials to be used, and based on the conditions for a known desulfurization-fluorination reaction.

Following each reaction scheme below, it is also possible to use the complex of the present invention as a fluorinating agent in a synthetic reaction of fluoroglucosides, based on fluorination of thioglycosides.

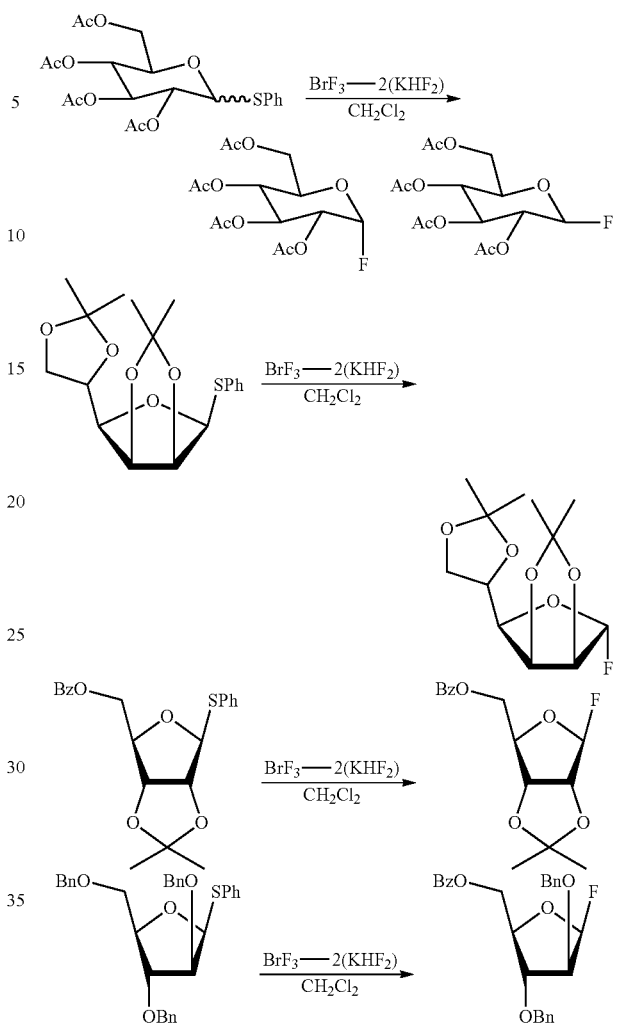

In each reaction scheme above, Ac represents acetyl, Ph represents phenyl, Bz represents benzoyl, and Bn represents benzyl.

The above reaction may also be performed in a nonpolar solvent, such as methylene chloride, chloroform, hexane, heptane, pentane, cyclohexane, benzene, chlorobenzene, toluene, and xylene. Specific reaction conditions may also be set according to, for example, the type of the starting materials to be used, and based on the conditions for a known desulfurization-fluorination reaction.

(3) Denitrification-Difluorination Reaction

The complex of the present invention may also be used as a fluorinating agent in denitrification-difluorination reactions. For example, following the reaction scheme below, a gem-difluoride is obtained by reacting the fluorinating agent with a ketone hydrazone compound.

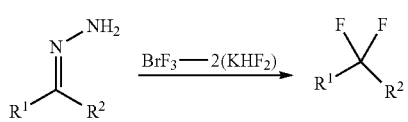

In the reaction scheme above, $R^1$ and $R^2$ are identical or different, and each represents substituted or unsubstituted phenyl, hydrogen, or lower alkyl. $R^1$ and $R^2$, taken together, may form a cyclic structure. $BrF_3$-2($KHF_2$) represents a complex obtained by the reaction of 2 mol of $KHF_2$, per mol of $BrF_3$.

Examples of the "substituted or unsubstituted phenyl" represented by each of $R^1$ and $R^2$ include phenyl that may be substituted with one or more substituents selected from the group consisting of halogen, lower alkyl, alkoxy, ester, amide, and amino.

$R^1$ and $R^2$, taken together, may foam, for example, a divalent group, such as an alkylene chain (e.g., —$CH_2$—$CH_2$—$CH_2$—, —$CH_2$—$CH_2$—).

The above reaction may also be performed in a nonpolar solvent, such as methylene chloride, chloroform, hexane, heptane, pentane, cyclohexane, benzene, chlorobenzene, toluene, and xylene. Specific reaction conditions may be set according to, for example, the type of the starting materials to be used, and based on the conditions for a known denitrification-difluorination reaction.

(4) Addition Reaction to Olefin Compound

The complex of the present invention may also be used as a fluorinating agent in the addition of Br—F to olefin compounds. For example, following the reaction scheme below, a Br—F adduct is obtained by reacting the fluorinating agent with an olefin compound.

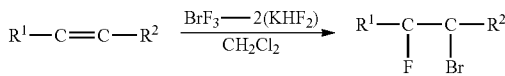

In the reaction scheme above, $R^1$ and $R^2$ are identical or different, and each represents hydrogen, alkyl, an ester residue (—$CO_2R$), or the like. $R^1$ and $R^2$, taken together, may form a cyclic structure. $BrF_3$-2($KHF_3$) represents a complex obtained by reacting 2 mol of $KHF_3$ with 1 mol of $BrF_3$.

$R^1$ and $R^2$, taken together, may form, for example, a divalent group, such as an alkylene chain (e.g., —$CH_2$—$CH_2$—$CH_2$—$CH_2$—, —$CH_2$—$CH_2$—$CH_2$—).

Electron-deficient olefins (e.g., $R^1$—C=C—$R^2$, in which $R^1$ and/or $R^2$ is an electron-withdrawing group, such as an ester) are usually unlikely to undergo the addition reaction. However, the use of the fluorinating reagent of the present invention allows the addition reaction to proceed, giving a target product with a sufficient yield. The following are examples of such a reaction: $CH_2$=$CHCO_2R \rightarrow CH_2BrCHFCO_2R + CH_2FCHBrCO_2R$. In the formula, R is alkyl.

The above reaction may also be performed in a nonpolar solvent, such as methylene chloride, chloroform, hexane, heptane, pentane, cyclohexane, benzene, chlorobenzene, toluene, and xylene. Specific reaction conditions may be set according to, for example, the type of the starting materials to be used, and based on the conditions for a known addition reaction to olefins.

Advantageous Effects of Invention

The complex of the present invention is useful as a fluorinating agent that has a high reactivity in fluorination reactions of various organic compounds. The complex of the present invention is an easy-to-handle substance because it has a low reactivity with, for example, methylene chloride, which is a general-purpose solvent, and is stable in air.

The complex of the present invention is thus a highly useful fluorinating agent in various fluorination reactions, such as desulfurization-difluorination reaction, desulfurization-fluorination reaction, denitrification-fluorination reaction, and addition reaction to olefins.

DESCRIPTION OF EMBODIMENTS

The following describes the present invention in more detail with reference to Examples. The symbols and abbreviations used in the Examples are as they are usually used in the chemical field, unless otherwise stated.

Example 1 (Production of Complex)

$KHF_2$ (5.17 g, 66 mmol) and $CH_2Cl_2$ (30 mL) were placed in a Teflon (registered trademark) container, and cooled to −78° C., followed by dropwise addition of $BrF_3$ (4.54 g, 33 mmol). While the temperature was maintained, the mixture was stirred for 30 minutes, and the temperature was increased to room temperature. The liquid portion was removed, and the solid portion was washed by adding 20 mL of $CH_2Cl_2$, the procedure of which was repeated three times. The resulting product was then stirred while nitrogen was blown in to obtain a complex ($BrF_3$-2$KHF_2$ complex) (8.84 g, 91%) as a solid by reacting 2 mol of $KHF_2$, per mol of $BrF_3$.

$^{19}F$-NMR (30 KHz) δ −10--65 (m), −150 (s).

The obtained complex was mixed with methylene chloride at room temperature; however, an exothermic phenomenon was not observed, and no reaction occurred. The exothermic decomposition onset temperature in nitrogen of the complex was measured by the method described above and was 197° C.

Example 2 (Production of Complex)

KF (2.5 g, 44 mmol) and $CH_2Cl_2$ (10 mL) were placed in a Teflon (registered trademark) container and cooled to −78° C., followed by dropwise addition of $BrF_3$ (3.0 g, 22 mmol). While the temperature was maintained, the mixture was stirred for 30 minutes, and the temperature was increased to room temperature. The liquid portion was removed, and the solid portion was washed by adding 5 mL of $CH_2Cl_2$, the procedure of which was repeated three times. The resulting product was then stirred while nitrogen was blown in to obtain a complex ($BrF_3$-2KF complex) as a solid by reacting 2 mol of KF, per mol of $BrF_3$.

$^{19}F$-NMR (30 KHz) δ −133 (s), −150 (s).

The obtained complex was mixed with methylene chloride at room temperature; however, an exothermic phenomenon was not observed, and no reaction occurred. The exothermic decomposition onset temperature in nitrogen of the complex was measured by the method described above and was 252° C.

Example 3 (Desulfurization-Difluorination Reaction)

The $BrF_3$-2$KHF_2$ complex (193 mg, 0.66 mmol) obtained in Example 1 and $CH_2Cl_2$ (2.4 mL) were placed in a Teflon (registered trademark) container. Then, compound 1a (100 mg, 0.3 mmol) shown in Table 1 below was added thereto at room temperature and stirred for 1 hour while the temperature was maintained. After the completion of the reaction, the resulting product was quenched with the addition of water, and after separation, the washing was performed with a saturated aqueous $NaHCO_3$ solution and a saturated aqueous $Na_2S_2O_3$ solution. The organic layer was dried over MgSO₄ and concentrated, followed by purification by silica column chromatography. In this manner, compound 2a (57 mg, 84%) shown in Table 1 below was obtained.

Examples 4 to 6 (Desulfurization-Difluorination Reaction)

The desulfurization-difluorination reaction was performed as in Example 3, except that compounds 1b to 1d shown in Table 1 below were used as the starting material in place of compound 1a used in Example 3, and that the molar ratio of the fluorinating agent to the starting material and the reaction time were changed to the values shown in Table 1. Table 1 shows the resulting products and their yields. In each table below, the values shown in the "Yield" columns are isolated yields, and the values in parentheses are yields calculated from F-NMR.

TABLE 1

| Ex. | Starting material | Molar ratio of fluorinating agent (to starting material) | Reaction time | Product | Yield (%) |
|---|---|---|---|---|---|
| 3 | 1a | 2.2 | 1 h | 2a | 84 |
| 4 | 1b | 3.0 | 15 min | 2b | 76 (85) |
| 5 | 1c | 3.0 | 15 min | 2c | 91 (99) |
| 6 | 1d | 2.2 | 3 h | 2c | (92) |

Example 7 (Desulfurization-Difluorination Reaction)

The desulfurization-difluorination reaction was performed as in Example 3, except that compound 1e shown in Table 2 below was used as the starting material in place of compound 1a used in Example 3, and that the molar ratio of the fluorinating agent to the starting material and the reaction time were changed to the values shown in Table 2. Table 2 shows the resulting product and the yield.

TABLE 2

| Ex. | Starting material | Molar ratio of fluorinating agent (to starting material) | Reaction time | Product | Yield (%) |
|---|---|---|---|---|---|
| 7 | MeO–C₆H₄–CH₂–C(=S)–OEt (1e) | 3.0 | 3.5 h | MeO–C₆H₄–CH₂–CF₂–OEt (2e) | (80) |

Examples 8 and 9 (Desulfurization-Fluorination Reaction)

The desulfurization-fluorination reaction was performed as in Example 3, except that compound 1f or 1g shown in Table 3 below was used as the starting material in place of compound 1a used in Example 3, and that the molar ratio of the fluorinating agent to the starting material, the reaction temperature, and the reaction time were changed to the values shown in Table 3. Table 3 shows the resulting products and their yields.

TABLE 3

| Ex. | Starting material | Molar ratio of fluorinating agent (to starting material) | Reaction conditions | Product | Yield (%) |
|---|---|---|---|---|---|
| 8 | Me₂C(C(SMe)₃)–C(=O)–OEt (1f) | 3.1 | 0° C., 1 h | Me₂C(CF₂SMe)–C(=O)–OEt (2f) | 81 |
| 9 | Me₂N–C₆H₄–C(SMe)₃ (1g) | 3.2 | 0° C., 15 min | Me₂N–C₆H₃(Br)–CF₃ (2g) | 52 (62) |

Examples 10 and 11 (Desulfurization-Fluorination Reaction)

The desulfurization-fluorination reaction was performed as in Example 3, except that compound 1h or 1i shown in Table 4 below was used as the starting material in place of compound 1a used in Example 3, and that the molar ratio of the fluorinating agent to the starting material and the reaction time were changed to the values shown in Table 4. Table 4 shows the resulting products and their yields.

TABLE 4

| Ex. | Starting material | Molar ratio of fluorinating agent (to starting material) | Reaction conditions | Product | Yield (%) |
|---|---|---|---|---|---|
| 10 | 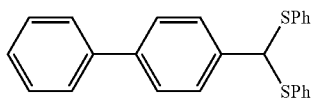<br>1h | 2.2 | Room temperature, 45 min | 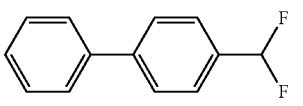<br>2h | 81 (90) |
| 11 | 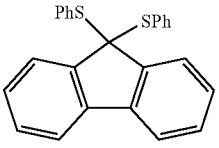<br>1i | 3.2 | Room temperature, 45 min | 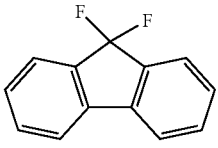<br>2i | (84) |

Example 12 (Desulfurization-Fluorination Reaction)

The desulfurization fluorination reaction was performed as in Example 3, except that compound 1j shown in Table 5 below was used as the starting material in place of compound 1a used in Example 3, and that the molar ratio of the fluorinating agent to the starting material and the reaction time were changed to the values shown in Table 5. The resulting product and the yield are shown in Table 5. The yield of the α-form was 52% while the yield of the β-form was 31%, and the total yield of both was 83%.

Example 12-2 (Desulfurization-Fluorination Reaction)

The desulfurization fluorination reaction was performed as in Example 3, except that compound 1j-2 shown in Table 5 below was used as the starting material in place of compound 1a used in Example 3, and that the molar ratio of the fluorinating agent to the starting material and the reaction time were changed to the values shown in Table 5. The resulting product and the yield are shown in Table 5. The yield of the α-form was 52% while the yield of the β-form was 31%, and total yield of both was 83%.

TABLE 5

| Ex. | Starting material | Molar ratio of fluorinating agent (to starting material) | Reaction conditions | Product | Yield (%) |
|---|---|---|---|---|---|
| 12 | 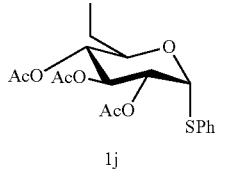<br>1j | 1.5 | 4 h | 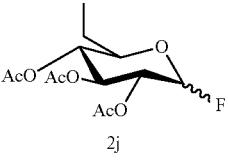<br>2j | 83 (86) (α:β = 52:31) |
| 12-2 | 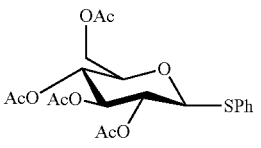<br>1j-2 | 1.5 | 4 h | 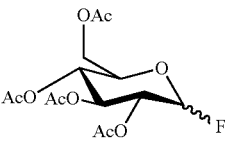<br>2j | 83 (86) (α:β = 52:31) |

Example 13 (Denitrification-Fluorination Reaction)

The desulfurization-fluorination reaction was performed as in Example 3, except that compound 1k shown in Table 6 below was used as the starting material in place of compound 1a used in Example 3, and that the molar ratio of the fluorinating agent to the starting material and the reaction time were changed to the values shown in Table 6. Table 6 shows the resulting product and the yield.

TABLE 6

| Ex. | Starting material | Molar ratio of fluorinating agent (to starting material) | Reaction time | Product | Yield (%) |
| --- | --- | --- | --- | --- | --- |
| 13 | 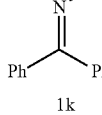<br>1k | 2.2 | 3.5 h | 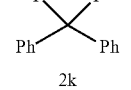<br>2k | 54 (73) |

Example 14 (Addition of Br—F to Olefin)

The BrF$_3$-2(KHF$_2$) complex (293 mg, 1 mmol) obtained in Example 1 and CH$_2$Cl$_2$ (5 mL) were placed in a Teflon (registered trademark) container. Then, compound 1l (68 mg, 0.5 mmol) shown in Table 7 below was added thereto at −40° C. and stirred for 24 hour while the temperature was maintained. After the completion of the reaction, the resulting product was quenched with the addition of water, and after separation, the washing was performed with a saturated aqueous NaHCO$_3$ solution and a saturated aqueous Na$_2$S$_2$O$_3$ solution. The organic layer was dried over MgSO$_4$ and concentrated, followed by purification by silica column chromatography. In this manner, compound 2l (58 mg, 50%) was obtained.

Example 15 (Desulfurization-Difluorination Reaction)

The desulfurization-difluorination reaction was performed as in Example 3, except that compound 1m shown in Table 8 below was used as the starting material in place of compound 1a used in Example 3, and that the molar ratio of the fluorinating agent to the starting material and the reaction time were changed to the values shown in Table 8. Table 8 shows the resulting product and the yield.

In the structural formula of compound 1m, Ar represents p-chlorophenyl.

TABLE 8

| Ex. | Starting material | Molar ratio of fluorinating agent (to starting material) | Reaction time | Product | Yield (%) |
| --- | --- | --- | --- | --- | --- |
| 15 | 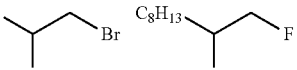<br>1m | 2.0 | 3 h | <br>2m | (84) |

Examples 16 to 18 (Desulfurization-Fluorination Reaction)

The desulfurization fluorination reaction was performed as in Example 3, except that compounds 1o to 1q shown in Table 9 below were used as the starting material in place of compound 1a used in Example 3, and that the molar ratio of the fluorinating agent to the starting material, the reaction temperature, and the reaction time were changed to the values shown in Table 9. Table 9 shows the resulting products and their yields.

TABLE 7

| Ex. | Starting material | Molar ratio of fluorinating agent (to starting material) | Reaction conditions | Product | Yield (%) |
| --- | --- | --- | --- | --- | --- |
| 14 | 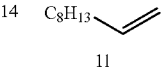<br>1l | 2.0 | −40° C., 24 h | <br>2:1<br>2l | 50 |

TABLE 9

| Ex. | Starting material | Molar ratio of fluorinating agent (to starting material) | Reaction conditions | Product | Yield (%) |
|---|---|---|---|---|---|
| 16 | 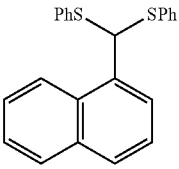<br>1o | 2.2 | Room temperature, 45 min | 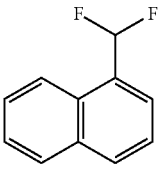<br>2o | (91) |
| 17 | 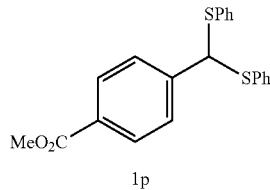<br>1p | 2.2 | Room temperature, 15 min | 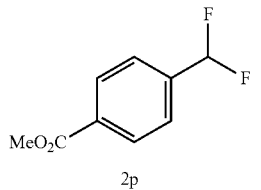<br>2p | 91(99) |
| 18 | 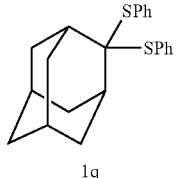<br>1q | 2.2 | 0° C., 60 min | 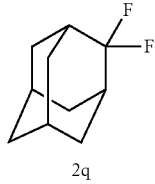 [SMILES: FC1(F)C2CC3CC(C2)CC1C3]<br>2q | (81) |

Examples 19 to 21 (Desulfurization-Fluorination Reaction)

The desulfurization-fluorination reaction was performed as in Example 3, except that compounds 1r to 1t shown in Table 10 below were used as the starting material in place of compound 1a used in Example 3, and that the molar ratio of the fluorinating agent to the starting material, the reaction temperature, and the reaction time were changed to the values shown in Table 10. Table 10 shows the resulting products and their yields.

TABLE 10

| Ex. | Starting material | Molar ratio of fluorinating agent (to starting material) | Reaction conditions | Product | Yield (%) |
|---|---|---|---|---|---|
| 19 | 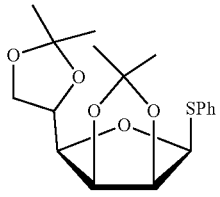<br>1r | 1.1 | 0° C., 15 min | 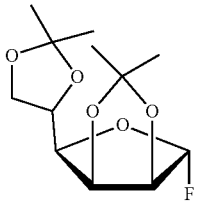<br>2r | 89 (94) |

TABLE 10-continued

| Ex. | Starting material | Molar ratio of fluorinating agent (to starting material) | Reaction conditions | Product | Yield (%) |
|---|---|---|---|---|---|
| 20 | 1s | 1.1 | Room temperature, 15 min | 2s | 87 |
| 21 | 1t | 1.1 | Room temperature, 15 min | 2t | (66) |

Example 22 (Desulfurization-Fluorination Reaction)

The desulfurization fluorination reaction was performed as in Example 3, except that compound 1u shown in Table 11 below was used as the starting material in place of compound 1a used in Example 3, and that the molar ratio of the fluorinating agent to the starting material, the reaction temperature, and the reaction time were changed to the values shown in Table 11. Table 11 shows the resulting product and the yield.

TABLE 11

| Ex. | Starting material | Molar ratio of fluorinating agent (to starting material) | Reaction conditions | Product | Yield (%) |
|---|---|---|---|---|---|
| 23 | 1u | 3.2 | 0° C., 15 min | 2u | 76 (83) |

The invention claimed is:

1. A method for fluorinating a compound, the method comprising:
bringing the compound into contact with a complex consisting of bromine trifluoride and at least one metal halide selected from the group consisting of halogenated metals and halogenated hydrogen metals.

2. The method according to claim 1, wherein the complex exhibits an exothermic decomposition onset temperature in nitrogen of 40° C. or higher.

3. The method according to claim 1, wherein the complex is a reaction product obtained by mixing bromine trifluoride with at least one metal halide selected from the group consisting of halogenated metals and halogenated hydrogen metals, in a nonpolar solvent.

4. The method according to claim 3, wherein the reaction product is obtained by reacting 0.5 mol or more of the metal halide, per mol of bromine trifluoride.

5. The method according to claim 1, wherein the metal halide is at least one member selected from the group consisting of a halogenated metal represented by the formula: MX, wherein M is $M^1$ or $(M^2)_{1/2}$), $M^1$ is an alkali metal, and $M^2$ is an alkaline earth metal, and X is a halogen atom; and a halogenated metal represented by the formula: $MHX^2$, wherein M and X are as defined above.

6. The method according to claim 1, wherein the metal halide is at least one potassium halide selected from the group consisting of halogenated potassium and halogenated hydrogen potassium.

7. The method according to claim 1, wherein the metal halide is at least one potassium fluoride selected from the group consisting of fluorinated potassium and fluorinated hydrogen potassium.

* * * * *